United States Patent [19]

Minarik et al.

[11] 4,150,563

[45] Apr. 24, 1979

[54] METHOD OF AND APPARATUS FOR THE RECIRCULATION OF FLUIDS IN A CLOSED CIRCUIT

[75] Inventors: Milan Minarik; Milan Popl; Jiri Mostecky, all of Prague, Czechoslovakia

[73] Assignee: Vysoka skola chemicko-technologicka, Prague, Czechoslovakia

[21] Appl. No.: 851,783

[22] Filed: Nov. 15, 1977

[51] Int. Cl.² ............................................. G01N 31/08
[52] U.S. Cl. ............................. 73/61.1 C; 73/422 GC; 210/198 C
[58] Field of Search ..................... 73/61.1 C, 422 GC; 210/34, 198 C

[56] References Cited

U.S. PATENT DOCUMENTS

| | | | |
|---|---|---|---|
| 3,747,630 | 7/1973 | Hurrell | 73/422 GC X |
| 3,885,439 | 5/1975 | Stone | 73/422 GC |
| 4,068,528 | 1/1978 | Gundelfinger | 73/422 GC |

*Primary Examiner*—Richard C. Queisser
*Assistant Examiner*—Joseph W. Roskos

[57] ABSTRACT

Method of and apparatus for liquid recirculation in at least substantially closed circuit which is particularly suitable for recycled liquid chromatography. The circulating liquid is brought into motion in the circuit inlet by working fluid supplied under pressure, e.g. from a pump, pressure gas cylinder, or the like. Circulating liquid approaching the end of the circuit beyond the circuit outlet is mechanically and at regular intervals repeatedly transported in the form of slugs into the beginning of the circuit in advance of the circuit inlet where the slugs are again forced into the circuit inlet by means of working fluid. The injection of one slug into the circuit inlet and the pushing of the following slug of equal volume out from the circuit outlet are carried out simultaneously.

5 Claims, 5 Drawing Figures

METHOD OF AND APPARATUS FOR THE RECIRCULATION OF FLUIDS IN A CLOSED CIRCUIT

The present invention relates to a method of and an apparatus for recycling fluids in a closed loop by means of a pump or another source of pressurized fluid such as, for example, a gas cylinder or the like, arranged outside such loop. The invention is advantageously used in liquid chromatography.

In order to separate perfectly difficultly separable components by liquid chromatography, it is often necessary to use extremely long chromatographic columns; this increases the pressure gradient to be overcome by a pump. Economic consequences of such a process are higher costs because of the column length and the necessity of a high-pressure pump, the price of which is at least several times of that of a low-pressure pump. Finally, another consequence is a substantially higher consumption of solvent for individual analyses, which, apart from the additional increase in expense of the process, entails the risk of fire in the manipulation of large quantities of such easily inflammable materials, which the most widely used solvents are. All the above disadvantages of operation on long chromatographic columns clearly point to the use of a recycling process in liquid chromatography, namely in the gel permeation mode.

In recycled circulation chromatography a mobile phase is again transported from the column outlet to its inlet so as to prevent any perceivable dilution, or re-intermixing of separated components of the analyzed mixture. This requires that the hydraulic channel extending from the column outlet to the inlet thereof be as short as possible and have a minimun volume. In practice, the recycling is carried out in two different ways, e.i. (1) by installing a pump with a relatively small internal volume between the outlet and the inlet of the column for which a piston, or peristaltic pump can be used and (2) by alternate pumping performed by switching the flow of the mobile phase by means of one or more multi-way valves installed between two columns, a pump and waste, so that a portion of the mobile phase containing the components to be analyzed will always be conveyed from the outlet of one column to the inlet of the other column; this process is not recycling in the best sense of the word, but rather a periodic disconnection of the column through which the analysed components pass and a re-connection of this column behind the column after the analyzed components have passed through it. The second mode (2) is more advantageous than the first, since the hydraulic channels connecting the two columns can have a practically unlimitedly small internal volume, so that by recycling the analyzed compounds the peak volume is not greater than in the case of the passage through an adequate column series. Another advantage of process (2) is the possibility of using any type of pump since the components to be separated do not pass through the pump. On the contrary, an essential disadvantage of the alternate pumping principle is the necessity of having a longer column relative to that used when recycling with a pump interconnected in a closed loop, as well as the dependence of valve switching upon the course of the chromatographic analysis; this mode makes any automation of the process of separating non-pretested mixtures impossible.

Since commercial liquid chromatographs are constructed so as to automatize a principally simple chromatographic process, the apparatuses equipped for recycling almost exclusively use the closed-loop pumping system with piston pumps interconnected in a circuit, (peristaltic pumps, which are theoretically perfect, are unusable for these purposes for many practical reasons such as poor resistance to organic solvents, relatively low working presure, and short lifetime of the pumping tubes). The closed-loop pumping method is, however, imperfect in that relatively narrow zones of the separated components become diluted during their passage through a piston pump and are partially intermixed. To achieve acceptable limits of dispersion in the chromatographic zone, the total internal volume of the pumping head should be as small as the dead volumes or capacities of the other parts of the chromatographic circuit, e.i. about 10 $\mu$l, which in the case of a piston pump designed to yield a flow rate of from 0.1 to 20 ml/min. would surpass the boundary of the present technical possibilities, apart from a considerably expense of such a technical solution.

Recycling in accordance with the present invention has advantages over both the above described modes (1) and (2). The mobile phase is continually and automatically transported from the column outlet to its inlet without passing through a space having a greater volume where a dispersion of the chromatographic zones might occur. A pump or another suitable source of pressurized fluid may act as the driving force to circulate liquid through the circulation circuit; the pump is connected to the circuit by a circulation valve located between the pump and the circuit in such a way that in certain period of (a) regular and fluent or (b) abrupt motion of a valve core with respect to a valve body one channel of the movable valve core of which connects the supply of working pressurized fluid leaving the pump with the circuit inlet, and the second channel of the movable valve core or element simultaneously connects the outlet of the circuit with the tubing withdrawing the working fluid.

The circulation valve is constructed as a multiway valve with a self-acting motion having at least four connecting tubings which, in open position, form two interconnecting paths which are always simultaneously interconnected by two neighboring channels of the valve core. The motion of the valve core with respect to the valve body is (a) regular and fluent or (b) abrupt, and individual connecting tubings of the valve are oriented such that the same end of the connecting channel of the valve core during one period of the interconnection adjoins the outlet of the circuit, and during the next period adjoins the circuit inlet. When a certain velocity or frequency of mechanical valve core channel switching from the position interconnecting the circuit outlet with the fluid withdrawal to the position interconnecting the supply of working pressurized fluid with the circuit inlet is exceeded, the volume of the circulating liquid forced out from the circuit outlet into a certain volume of the interconnecting valve core channel during one period of interconnection is equal to the volume of circulating liquid forced out into the circuit inlet during the following period of interconnection from the same channel.

The resulting effect is a systematic closure of the circulation circuit and the transportation of circulating liquid from the circuit outlet to the circuit inlet without passing through the pump or through another space greater than the volume of the capillary or small tubing connecting the outlet and inlet of an imaginary optimum circulation circuit. The process can be looked upon as the special case of a continual regular sample injection of all of the eluate from the column outlet into its inlet. In order to attain maximum efficiency, the channel diameter has, of course, to be equal to or less than the diameter of the small tubings or capillaries by which columns are connected to the circulation valve. Then the piston type liquid flow is facilitated, and the least dispersion of chromatographic zones occurs.

Further, the elimination of the transfer of pressure pulses from the pump to the circulation valve is desirable; thus the use of a pulseless pump is suitable. When single piston pumps are used, the addition of a pulse damper is recommended. The efficiency of recycling using narrow columns or columns with a high separation efficiency (large number of plates) having a small volume of the individual chromatographic zones can be decreased by the reversal of the concentration gradient in piston-like sections of circulating liquid (slugs) inside the circulation valve. In order to avoid this phenomenon, the two-fold reversal of the concentration gradient in accordance with the second embodiment disclosed herein can be employed, and the individual slugs containing fragments of the chromatographic zone then enter the column with the orientation of the concentration gradients being the same as in the column outlet.

The means for revolving the core of the circulation valve may be a stepping motor with a fast motion between individual steps; such valve driving means is better suited than is a constant speed driving means, the use of which may give rise to pressure pulses which may be transferred to the column, the packing of which is not effective enough to avoid leakages. The losses of circulating liquid, and therefore losses of separated components, resulting from the passage of circulating liquid into working fluid (this is mostly identical with circulating liquid) as a consequence of partial mixing at the boundary (or at an imaginary boundary) of their contact inside the channels of the core of the circulation valve can be neglected if the frequency of recycling is small. Should the losses be obvious with a higher frequency of recycling, they can be, to some extent, altered by changing the length of the channels of the core of the circulation valve, or they can be eliminated by the empirical correction of the apparatus.

The essence of the invention is the provision of a novel mode of liquid circulation in a closed circuit which is suitable particularly for recycling liquid in chromatography where the working fluid (gas or liquid) supplied under pressure (e.g. from a pump, a pressure cylinder, or the like) puts the circulating liquid into motion in the circuit inlet; the invention is based on the fact that circulating liquid approaching the end of the circuit is mechanically and at regular intervals repeatedly transported in the form of slugs into the beginning of the circuit, where the slugs are again pushed into the circuit inlet by means of working fluid, the injecting of one slug into the circuit inlet and the pushing of the following slug of equal volume from the circuit outlet being carried out at the same time.

The herein disclosed mode of liquid recirculation of the invention is realized by an arrangement consisting of a valve core with a number of interconnecting channels that is accommodated in the valve body in which both the supply and withdrawal tubings of working fluid and also the inlet and outlet tubings of circulating liquid are located, the supply tubing of working fluid and the inlet tubing of circulating liquid being interconnected at one period by one interconnecting channel of the valve core and at the same time the tubing for withdrawing the working fluid and the outlet tubing for the circulating liquid being interconnected by the neighboring interconnecting channel of the valve core. The valve core is movable in the valve body and is connected to be driven by a source of periodic motion so as to move the interconnecting channels from the position of the axis of the outlet to that of the axis of the inlet. The valve body can be of cylindrical shape and the axes of the interconnecting channels can lie on a circle co axial with the cylindrically shaped valve core, the source of periodic motion then being created by a rotatable driving means. Alternatively, the valve core can reciprocate.

The arrangement of the circulation valve can be made also in such a way, that four opposite outlets issue from the valve body along the axes of four adjacent interconnecting channels, and from the four outlets situated on one side the two outer outlets create the beginning and the end of the circulation circuit and the other two inner outlets are interconnected by a short connection having the least internal volume, while, on the opposite side there is disposed the tubing for the withdrawal of working fluid opposite to the outlet of the circulation circuit, and next to it there are disposed the tubing for the supply of working fluid and further the other two outlets, which are connected by a loop. Hence, when the valve is in its interconnecting position, the pressure from a pump is transferred by the tubing supplying working fluid via the interconnecting channel and further via a short loop on the side of the circulation circuit back through the further channel into a loop on the side of the working fluid and from here back again through the last channel into the beginning of the circulation circuit.

Said valve core can be also provided with only two interconnecting channels and be of rectangular shape where the supply tubing of working fluid is disjoined and the opposite inlet tubings lead, after their re-joining, into the circuit, the outlet of circulating liquid between both the inlet arms being attached via the interconnecting channel in the core with the withdrawal tubing of working fluid. The valve core driving means is then provided by a straight-motion reverse driving arrangement.

Preferred embodiments for liquid recycling in accordance with the invention are illustrated in the accompanying drawings.

Figure 1:
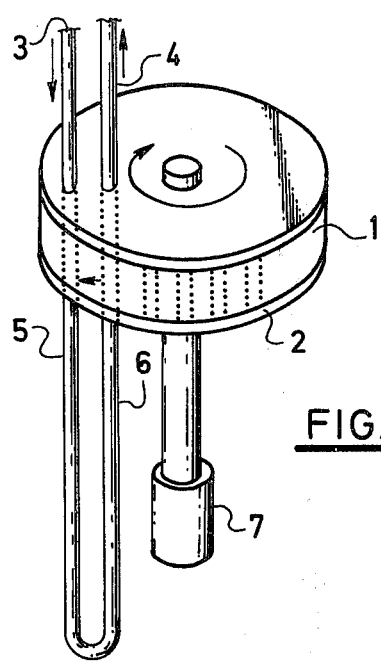
FIG. 1 is a view in perspective of a cylindrically shaped embodiment of valve for recycling liquid in chromatography with a source of rotary motion.

In FIG. 1 there is shown a valve core 1 having a set of interconnecting channels spaced apart around its periphery, the core 1 being accommodated in a valve body 2. In the valve body 2 there are provided, in opposite positions, coaxial small tubings: a capillary 3 for the supplying of working fluid with an inlet capillary 5 for circulating liquid, and a capillary 4 for withdrawing working fluid with a capillary 6 for the outlet of circulating liquid. The transportation of circulating liquid between the outlet 6 and the inlet 5 is provided for by the rotation of the core in a clockwise direction, such rotation being caused by a source of periodic motion 7. The core 1 is made, for instance, of polyimide, polyformaldehyde, or polytetrafluoroethylene filled with glass fibers and molybdenum tetrasulfide, or the like. The valve body 2, which is preferably made of stainless steel, has the shape of a hollow cylinder having a bottom, houses the core 1 to which it is sealed by means of a thrust sealing disc constituting the upper portion of the valve body 2. To facilitate the sealing of the boundary surface between the valve core 1 and the valve body 2, said surface can be variously shaped, while the channels in the valve core 1 can optionally be bent or curved. The source of periodic motion 7 can be either a motor having a constant speed of rotation coupled directly, or preferably, via a cam to the valve core causing an abrupt or jump running of the valve core, or stepping motor the steps of which correspond to the interconnection positions of the core 1 relative to the valve body 2.

Figure 2:
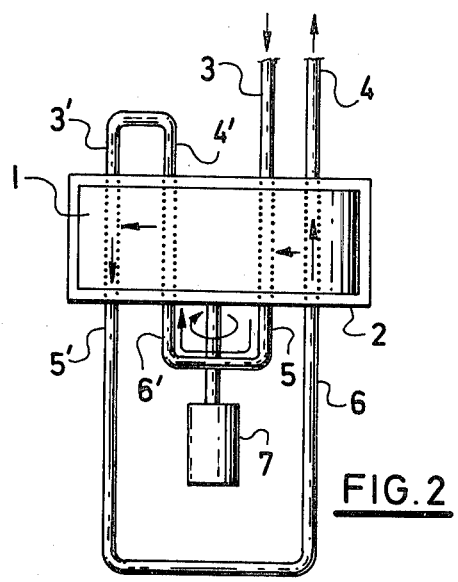
FIG. 2 is a view in elevation of the embodiment of FIG. 1 with connecting tubings for the reversal of the concentration gradient in the transported slugs of circulating liquid into its original direction.

FIG. 2 illustrates an alternative embodiment in which the inlet 5 is re-connected with an additional outlet 6' and the pressure transfer from said additional outlet 6' to an additional inlet 5' is provided for by a loop formed by an additional withdrawal tubing 4' and an additional supply tubing 3'.

Figure 3:
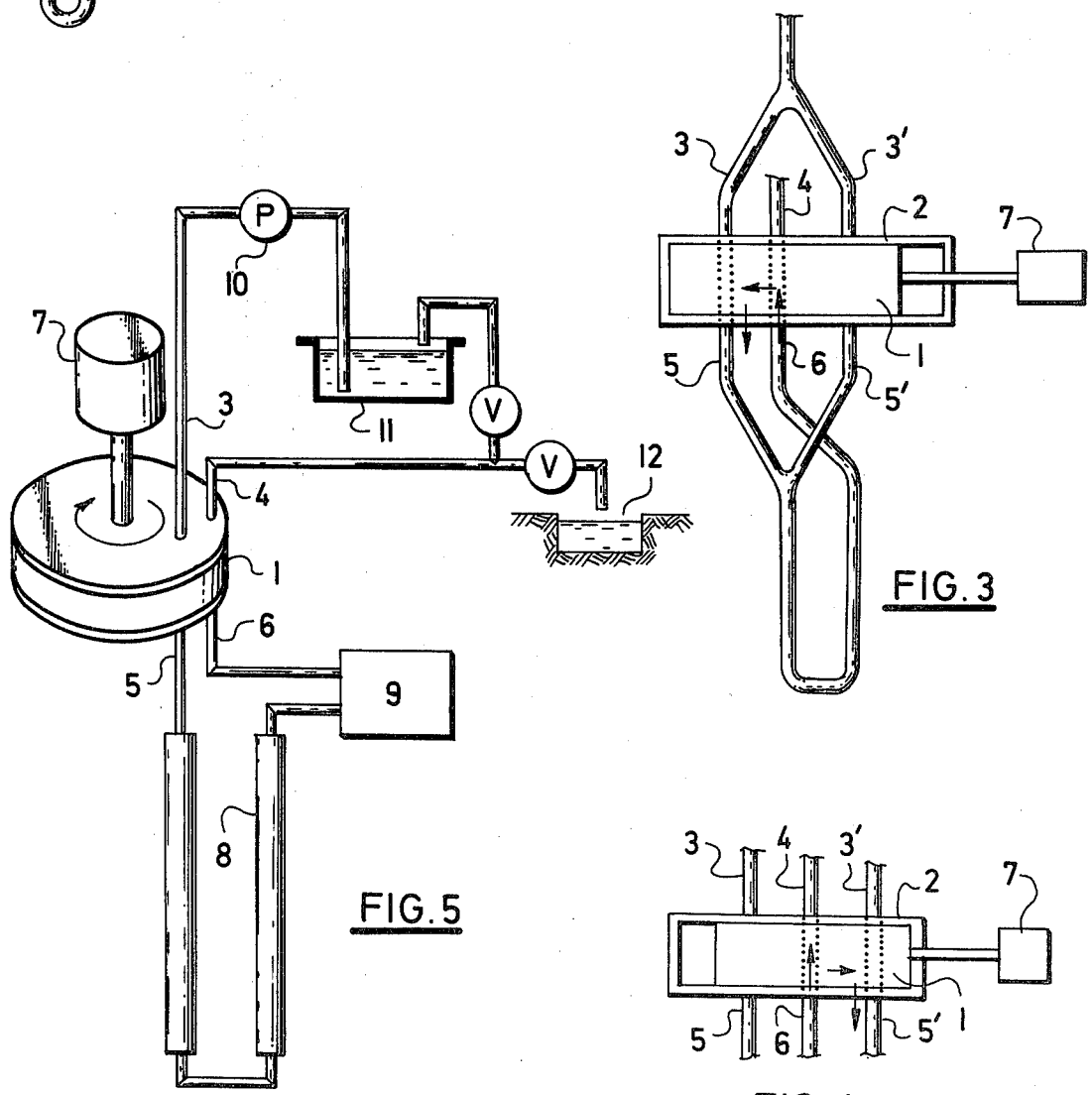
FIG. 3 is a view in elevation of a second, rectangularly shaped, reciprocating embodiment of valve for circular chromatography, the valve being provided with a vibratory source of motion.
Figure 4:
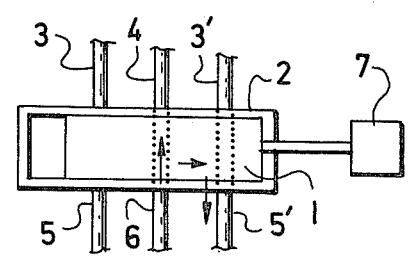
FIG. 4 is a view in elevation showing the second working position of the valve core of FIG. 3 with respect to the valve body, such second position being opposite to the position illustrated in FIG. 3.

In the embodiment shown in FIGS. 3 and 4 wherein the valve core reciprocates, the inlet tubing is formed with two short capillaries 5 and 5' while the source of motion 7 generates vibrations in the direction perpendicular to the channel axis, that is, horizontally in FIGS. 3 and 4. As in FIGS. 1 and 2, reference character 1 designates the valve core, 2 designates the valve body, and 7 designates the valve core driving means, which in this case reciprocates the valve core. Working fluid enters the valve through tubing 3 or 3' and leaves it through tubing 4. The inlet tubing has branches 5 and 5'.

FIG. 3 illustrates a first operative position of the valve core, whereas FIG. 4 shows the second operative position of the embodiment shown in FIG. 3. In the position of the core shown in FIG. 3, tubing 3 is in communication with inlet capillary 5, whereas in FIG. 4 tubing 3' is in communication with inlet capillary 5'.

Figure 5:
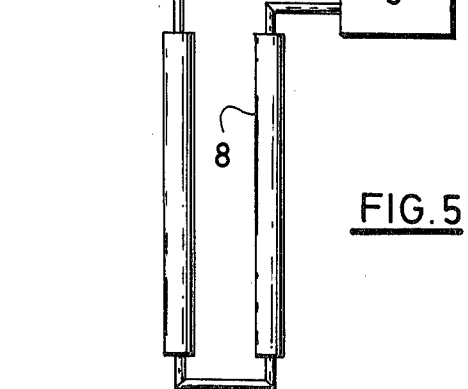
FIG. 5 is a general schematic view of a chromatograph in accordance with the invention.

FIG. 5 is a general schematic view of the chromatograph of the invention for recirculation of liquids within a closed circuit. The apparatus consists of a recirculating circuit comprising a column 8, a detector 9, a valve with a valve core 1 and a body, an inlet tubing 5, and an outlet tubing 6. As a source of the pressurized fluid, a pump 10 is used. The pressurized fluid is either returned to a reservoir 11 or discharged to a sump 12.

In the operation of the apparatus of FIG. 5, the source of a discontinuous, such as oscillartory, motion rotates the core 1 in the direction of the arrow. In such a way, the individual slugs of the liquid pushed from the detector 9 into the interconnecting channel of the core 1 through the outlet tubing 6, are transferred to an inlet position between the supply tubing 3 and the inlet tubing 5 where, due to the action of the pump 10, they are pushed again to the inlet tubing 5 of the column 8. The ratio of the rate of the liquid flow through the column 8, and volume of the interconnecting channels in the core 1, as well as the frequency of the discontinuous motion generated by the source 7 are duly proportioned to prevent the recirculated liquid from passing from the outlet tubing 6 to the withdrawal tubing 4 and to cause it to fill only a part of the total capacity of the respective interconnecting channel of the core 1 during each step. The rate of flow through the column 8 and the frequency of the discontinuous motion source 7 are constant, in order that the volume of liquid slug forced out from the outlet tubing during one period is identical to that injected into the inlet tubing during the following period.

As to the production and constructional details of the circulation valve, and especially the manner of sealing of its sliding areas, the experience acquired from the construction of multiway valves currently used in liquid chromatography can be broadly applied. The dissimilarity of the rotary and reciprocatory valves consists only in shape, geometry and number of channels, alternatively also in number of connecting tubings, but the principle remains the same in both embodiments. In contrast to other valves used in liquid chromatography, the valve-sealing requirements of the circulation valve are less, for one of the reasons by recycling is used is the pressure decrease in the column inlet produced by the shortening of the required column length.

It follows that the invention enables circular liquid chromatography (and principally also gas chromatography) to be performed by means of constructionally modest facilities. The degree of automation achieved is the same as that possessed by the best prior processes and arrangements. Moreover, the invention yields significantly higher quality or efficiency expressed by the magnitude of enlargement of the chromatographic zone and the smaller cost of the facilities needed to practise the invention.

Although the invention is illustrated and described with reference to a plurality of preferred embodiments thereof, it is to be expressly understood that it is in no way limited to the disclosure of such a plurality of preferred embodiments, but is capable of numerous modifications within the scope of the apended claims.

What is claimed is:

1. In a method of liquid recirculation in an at least substantially closed circuit having a circuit inlet and a circuit outlet by moving the circulating liquid into the inlet of the circuit by working fluid supplied under pressure to the circuit, the improvement which comprises mechanically and at regular intervals repeatedly transporting circulating liquid approaching the end of the circuit beyond the circuit outlet in the form of slugs of equal volume into the beginning of the circuit in advance of the circuit inlet, and again pushing these slugs into the circuit inlet by means of working fluid, the injection of one slug into the circuit inlet and the pushing of the following slug out of the circuit outlet being carried out simultaneously.

2. In apparatus for recirculating liquid in an at least substantially closed circuit having a circuit inlet and a circuit outlet by moving the circulating liquid into the inlet of the circuit by working fluid supplied to the circuit under pressure, the improvement which comprises a valve interposed in the circuit, the valve having a body and a valve core movably disposed in the valve body, the valve core having a set of channels extending therethrough, means for driving the valve core from a first operative position to a second operative position, the valve body having supply and withdrawal ports for the working fluid, tubings connected to said supply and withdrawal ports for the working fluid, the valve body further having circuit inlet and outlet ports for the circulating liquid, tubings connected to the circuit inlet and outlet ports of the valve body, the supply port for the working fluid and the inlet port for the circulating liquid lying on the axis of a first channel of the valve core and the withdrawal port for the working fluid and the outlet part for the circulating liquid lying simultaneously along the axis of a second neighboring channel of the valve core.

3. Apparatus as claimed in claim 2, in which the valve core is of circular cylindrical shape, the means of driving the valve core oscillates the core between two operative positions with a periodic motion, and the axes of the channels in the valve core lie on a circle coaxial with the valve core.

4. Apparatus as claimed in claim 2 in which the valve body for four sets of axially aligned inlet and outlet ports, the valve core has four channels therethrough, and the ports in the valve body and the channels in the valve core are so arranged that in one position of the valve core it provides communication therethrough between the respective inlet and outlet ports of the valve body, in said one position of the valve core working fluid passing through the valve by way of a first inlet port, a first channel in the valve core, and a first outlet port, the working fluid then passing through a first tubing into a second inlet port, through a second inlet port to the valve body through a second channel in the valve core, and through a second outlet port in the valve body into a second tubing, the working fluid then passing into a third inlet port in the valve body, to a third channel in the valve core and through a third outlet port into a third tubing, the working fluid then passing from the third tubing into a fourth inlet port in the valve body, through a fourth channel in the valve core and thence outwardly from the valve through a fourth outlet port.

5. Apparatus as claimed in claim 2, in which the set of channels in the valve core is provided with two channels therethrough, the valve core reciprocates between two positions thereof, the valve body is provided with three sets of respective inlet and outlet ports, the working fluid supply tubing is divided into two branches connected, respectively, to the first and third inlet ports of the valve body, the withdrawal tubing for the working fluid having two branches, one of which is connected to the first outlet port of the valve and the other of which, is connected to the third outlet port of the valve body, the parts being so constructed and arranged that in a first operative position of the valve core, one channel therein provides communication between the second inlet and the second outlet port of the valve body, and the other second channel in the valve core provides communication between the third inlet port and the third outlet port of the valve body, and in the other operative position of the valve core, the said one channel therein provides communication between the first inlet port and the first outlet port of the valve body and the other second channel in the valve core provides communication between the second inlet port and the second outlet port, and wherein the means for driving the valve core reciprocates it with periodic harmonic motion.

* * * * *